(12) United States Patent
Scott (10) Patent No.: US 8,709,712 B2
(45) Date of Patent: Apr. 29, 2014

(54) METHOD FOR IDENTIFYING BACTERIA IN A SAMPLE

(75) Inventor: Lesley Erica Scott, Randburg (ZA)

(73) Assignee: University of Witwatersrand, Johannesburg, Johannesburg (ZA)

( * ) Notice: Subject to any disclaimer, the term of this patent is extended or adjusted under 35 U.S.C. 154(b) by 0 days.

(21) Appl. No.: 13/696,403

(22) PCT Filed: May 6, 2011

(86) PCT No.: PCT/IB2011/052016
§ 371 (c)(1), (2), (4) Date: Nov. 6, 2012

(87) PCT Pub. No.: WO2011/138765
PCT Pub. Date: Nov. 10, 2011

(65) Prior Publication Data
US 2013/0052645 A1    Feb. 28, 2013

(30) Foreign Application Priority Data
May 6, 2010  (ZA) .................... 2010/03215

(51) Int. Cl.
*C12Q 1/00* (2006.01)
*G01N 33/53* (2006.01)
*G01N 33/554* (2006.01)

(52) U.S. Cl.
USPC .................. 435/4; 435/7.2; 435/7.32

(58) Field of Classification Search
None
See application file for complete search history.

(56) References Cited

U.S. PATENT DOCUMENTS

| 5,759,798 A | 6/1998 | Dunlap |
|---|---|---|
| 2010/0021878 A1 | 1/2010 | Kim et al. |
| 2011/0217694 A1 * | 9/2011 | Buzatu et al. ............. 435/5 |

OTHER PUBLICATIONS

Burdz et al (Diagnostic Microbiology and Infectious Disease vol. 47, pp. 503-509, 2003).*
Saito et al., J Infect Chemother 11:220-25 (2005).
Pina-Vaz et al., J of Clincal Microbiology, 42(2): 906-08 (2004).
Cohen and Sahar, J of Clinical Microbiology, 27(6): 1250-56 (1989).
Rajwa et al., Cytometry, 73A(4): 369-79 (2008).
International Search Report for International Application No. PCT/IB2011/052016 mailed Aug. 8, 2011 by European Patent Office.

* cited by examiner

*Primary Examiner* — Albert Navarro
(74) *Attorney, Agent, or Firm* — RatnerPrestia (57) ABSTRACT

This invention describes a method for identifying bacteria. In particular, this invention relates to a method for identifying and quantifying mycobacteria from a sputum sample taken from a subject using flow cytometry. Further described is the use of flow cytometry to identify and quantify *Mycobacterium tuberculosis* from sputum-derived samples. Once identified and quantified, the samples are spotted onto filter cards for use in verification of an existing method of diagnosis, calibration of an existing method of diagnosis and/or the establishment of an external quality control system for use in conjunction with these methods of diagnosis. In one embodiment the method is used to diagnose tuberculosis (TB).

8 Claims, 6 Drawing Sheets

METHOD FOR IDENTIFYING BACTERIA IN A SAMPLE

This is a U.S. national application of International Application PCT/IB2011/052016, filed May 6, 2011, which claims priority to South Africa No. 2010/03215, filed May 6, 2010, the contents of each of which applications are incorporated herein by reference in their entireties for all purposes.

BACKGROUND OF THE INVENTION

This invention describes a method for identifying bacteria. In particular, this invention relates to a method for identifying and quantifying mycobacteria from a sputum sample using flow cytometry. Further described is the use of flow cytometry to identify and quantify *Mycobacterium tuberculosis* from sputum-derived samples for verification, calibration and/or the establishment of a quality control system for use during diagnosis of tuberculosis (TB).

Despite the identification of *M. tuberculosis* as the cause of TB more than a century ago, diagnosing TB in resource poor countries remains a challenge, especially in people living with HIV. TB is the disease caused by infection of *M. tuberculosis*, which remains an important cause of morbidity and mortality, with over 9 million new cases and about 1.8 million deaths annually. Due to the contagious nature of the disease, rapid identification is crucial to minimise the transmission rate between individuals in communities and health care facilities.

The most common method for diagnosing TB in most countries is smear microscopy, which is cheap and relatively easy to perform, but has modest sensitivity (35 to 80%). The sensitivity of smear microscopy is especially poor in HIV-infected individuals and children, populations that comprise the majority of cases in many sub-Saharan African countries. The accepted gold standard for TB diagnosis is culture for *M. tuberculosis*. This method is highly sensitive and allows identification of *M. tuberculosis* and differentiation between drug-sensitive and drug-resistant strains, but it has many limitations. The greatest limitation is the turnaround time of 2 to 6 weeks, which reduces its usefulness in clinical decision-making. Another limitation is that for culture to be performed, it has to be carried out in a level of biosafety infrastructure (BSL 2 to 3) with particular laboratory operational requirements, which cannot be implemented easily in decentralized resource poor settings. Even with the use of liquid culture methods such as BACTEC™ MGIT960 and MGIT DST (BD Diagnostic Systems) there are still shortcomings in that the methodology is still "human resource" intensive, costly and prone to contamination. There has therefore recently been acceleration in the development of new TB diagnostic methods, especially with the need to prevent TB infection in the wake of the HIV pandemic.

According to the StopTB Partnership (http://www.stoptb.org/), current and new technologies for active and latent TB diagnosis can be divided into their use in reference laboratories, peripheral laboratories and clinic based settings (POC), and consists of several different types of technologies. These are:

(i) Nucleic Acid Amplification Tests (NAAT) for Multiple Drug Resistant (MDR)-TB diagnosis and speciation assay such as GenoType® MTBDR and MTBDRplus (Hain LifeSciences), INNO-LiPA Rif.TB (Capilia TB-Neo), GeneXpert MTB/RIF (Cepheid), loop-mediated isothermal amplification technology (TB-LAMP, Eiken Chemical Co), COBAS TaqMan MTB (Roche Molecular Systems), Gen-Probe Amplified *Mycobacterium tuberculosis* Direct Test (AMTD) and enhanced AMTF (E-AMTD, Gen-Probe), LightCycler *Mycobacterium* detection kit (LCTB) (Roche Applied Science), Seeplex TB Detection Kit (Seegene, Korea), BD-ProbeTec Direct and the semi-automated ProbeTec ET system (Becton Dickinson) and the Abbott LCx (Abbott Molecular).

(ii) Interferon Gamma Release Assays for diagnosis of latent *M. tuberculosis* infection (QuantiFERON®-TB Gold In Tube, T-SPOT.TB®) and the TB patch test also for the diagnosis of latent infection.

(iii) Antigen based assays such as lipoarabinomannan (LAM) and breathalyzer screening test for screening for TB.

(iv) Phage based tests for rapid diagnosis of MDR-TB.

(v) Other methods for detection of drug resistant *M. tuberculosis*: the calorimetric redox indicator method, Microscopic Observation Drug Susceptibility (MODS), nitrate reductase assay, and thin layer agar culture, bleach microscopy, sputum filtration, vital fluorescent staining of sputum stains for improved smear microscopy, light Emitting Diode (LED) fluorescence microscopy for improved direct smear microscopy.

Studies of patients in the HIV prevalent areas of sub-Saharan Africa have shown that the risk of tuberculosis incidence is 8.3 times higher for those who are infected with HIV than for those who are uninfected. Smear-negative tuberculosis is more common amongst HIV-positive persons, and is difficult to diagnose. The WHO has established algorithms for the diagnosis of smear negative TB in HIV-positive persons. Sputum PCR offers the potential for improved sensitivity compared to TB microscopy, although some variability has been reported 0.85 (range 0.36-1.00) and specificity of 0.97 (range 0.54-1.00). A new PCR method from Cepheid called the GeneXpert MTB/RIF, however, offers great promise since the first reports of sensitivity and specificity on smear-positive culture positive patients of 98.2% and smear-negative culture-positive patients of 72.5%. Furthermore, a study conducted by the Department of Molecular Medicine and Haematology with Witwatersrand Reproductive Health and HIV Research Unit (RHRU) on outpatient pulmonary adult TB patients, 70% of which were coinfected with HIV, revealed that the sensitivity of a single GeneXpert MTB/RIF test compared to a single BACTEC MGIT culture was 86%. This method is a real-time PCR based system that requires 2 minutes hands-on-time and generates a result within 2 hours, which also includes sensitivity or resistance to rifampicin. This system can be performed at the bedside by 'non-technically skilled' persons and does not require biosafety infrastructure. Limitations of this method, however, are high cost and its current modular format, i.e. the instrument design is presented as modules of 1-16, 32 and 48. The modules are currently limited to low throughput bedside testing or small laboratories, and solutions for high throughput laboratory testing, especially needed in large centres where there is high HIV/TB prevalence, are still urgently needed. Despite these limitations, the World Health Organisation has endorsed the use of the GeneXpert MTB/RIF assay in TB endemic countries and declared it a major milestone for global TB diagnosis.

In order for an endemic country's health system to implement the GeneXpert MTB/RIF assay in response to global health principles, a number of aspects require attention for functional implementation of this assay. These include: determining the main logistical and operational issues related to GeneXpert MTB/RIF implementation (e.g., cartridge supply, downtime of the GeneXpert unit); establishing a sample database for calibration and verification of the results obtained for each GeneXpert instrument installed (before the instrument is deemed acceptable for reporting patient results); and generating appropriate external quality assessment (EQA) programs to ensure on-going quality testing in both laboratory and non-laboratory settings.

It is anticipated that based on the specific GeneXpert MTB/RIF assay characteristics, verification and EQA programs will require the following criteria: 1) testing material must contain whole *M. tb* for capture in the GeneXpert MTB/RIF cartridge; 2) transportation of EQA material needs to be safe; 3) the testing procedure needs to be safe and compatible with the GeneXpert MTB/RIF current testing protocol; non-laboratory skilled health care workers must be able to perform the testing in non-laboratory settings; and the programs will need to be cost effective and sustainable for national programs.

Apart from the technologies describe above and their associated shortfalls, the diagnosis of TB, via the identification and quantification of *M. tuberculosis*, in an HIV endemic area have several further complications and implications: HIV infection often leads to a reduction in sputum production and a reduction in good quality sputum. This leads to an increase in the number of smear negative culture positive cases. This in turn results in delayed diagnosis, which leads to an increased risk of transmission. In addition, diagnostic tests are required for screening of people living with HIV to aid in the eligibility assessment for preventive therapy, and diagnosis of TB in people eligible for antiretroviral treatment.

Therefore, the solution for TB diagnosis may become multifactorial in that clinical algorithms as well as applying different types of tests for different scenarios may be needed. In particular, there is a need for a rapid test for identifying the presence of *M. tuberculosis* in a sample taken from a patient (i.e. one which can provide a result within 24 hours) and which is relatively easy to perform and which is also affordable. Furthermore, there is a need to establish a reliable method, for use with the GeneXpert MTB/RIF assay, for generating a sample database for use in calibration and verification of the results obtained by this method and further for on-going external quality control assessment.

SUMMARY OF THE INVENTION

According to a first embodiment of the invention, there is provided a method of identifying the presence or absence of bacteria, the method including the step of:
performing flow cytometry on a sputum sample from a subject;
identifying the presence or absence of events within a region of increased angular fluorescence and increased angular side (SS) or forward scatter (FS) relative to a region of background debris in the sample.

The region of increased angular fluorescence and increased angular SS or FS relative to the background debris region may be seen at an angle of from about 40° to about 50° on a fluorescence versus side (or forward) scatter plot, and preferably at about 45°.

The region of increased angular fluorescence and increased angular SS or FS relative to the background debris region may be bacteria in the sample, preferably mycobacteria, such as *M. tuberculosis, M. smegmatis, M. bovis, M. avium, M. fortuitum* and so forth. Preferably, the mycobacteria is *M. tuberculosis*.

The absence of events within a region of increased angular fluorescence and increased angular SS or FS relative to the background debris region may be indicative that the subject does not have tuberculosis.

The presence of events within a region of increased angular fluorescence and increased angular SS or FS relative to the background debris region may be indicative that the subject has tuberculosis.

The subject may be a human or other animal.

The background debris may include lysed cells, mucous, saliva and the like, and is typically present in sputum samples from both tuberculosis-positive and tuberculosis-negative subjects.

The sputum sample may be liquefied and/or decontaminated and/or inactivated prior to performing the flow cytometry.

Preferably, the sputum sample is deactivated. The inactivation agents may be selected from the group comprising IDP, Xpert SR buffer, heat, and the addition of lysozyme.

The sputum sample may be treated with a nucleic acid binding dye, such as auramine O, SYTO dye or propidium iodide.

The flow cytometry may be performed using beads.

The bacteria may be pre-labelled with a bead, ligand and/or specific antibody, all of which may be fluorescently labelled and detected by flow cytometry, in order to aid the identification of events in the angular region.

The method may further include the step of liquefying and/or decontaminating and/or inactivating the sputum sample prior to performing the flow cytometry. The sputum sample may be cultured prior to liquefying and/or decontaminating and/or inactivating.

The method may also include the step of quantifying the identified bacteria.

Preferably, the quantified liquefied and/or decontaminated and/or inactivated sputum sample is spotted onto an absorbent material. The absorbent material may be selected from the group comprising a filter card, a filter paper, a swab, a bead, a sample tanker and cotton. The absorbent material ideally includes bacterial field strains, reference strains or negative controls. The absorbent material may find use in conjunction with any method of diagnosis of tuberculosis. In particular, the absorbent material may find use for verification of the method and/or calibration of the method and/or use as an external quality control assessment (EQA) tool.

The method of diagnosis may be selected from the group comprising GenoType® MTBDR and MTBDRplus™, INNO-LiPA™ Rif.TB, GeneXpert™ MTB/RIF, loop-mediated isothermal amplification technology, COBAS TaqMan™ MTB, Gen-Probe Amplified *Mycobacterium Tuberculosis* Direct Test (AMTD) and enhanced AMTF (E-AMTD), LightCycler™ *Mycobacterium* detection kit (LCTB), Seeplex TB Detection Kit, BD-ProbeTec Direct and the semi-automated ProbeTec ET system and the Abbott LCx.

In particular, the method of diagnosis is the GeneXpert MTB/RIF test.

In a second embodiment of the invention, there is provided a method of preparing an absorbent material including bacteria, the method including the steps of:
i) identifying and quantifying the bacteria according to the method described above; and
ii) spotting the identified and quantified bacteria onto the absorbent material.

The bacteria preferably include field strains, reference strains or negative controls.

In a third embodiment of the invention, there is provided an absorbent material including bacteria prepared according to the above-mentioned method.

In a fourth embodiment of the invention there is provided a method of identifying the presence or absence of bacteria and quantifying the bacteria, if present, the method including the steps of:

i) performing flow cytometry on a sputum sample from a subject;
ii) identifying the presence or absence of events within a region of increased angular fluorescence and increased angular side or forward scatter relative to a region of background debris in the sample;
iii) quantifying the bacteria present in the region of increased angular fluorescence and increased angular side or forward scatter relative to a region of background debris in the sample;
iv) spotting the quantified bacteria onto an absorbent material for use in any method of diagnosis of a disease.

The region of increased angular fluorescence and increased angular SS or FS relative to the background debris region may be seen at an angle of from about 40° to about 50° on a fluorescence versus side (or forward) scatter plot, and preferably at about 45°.

The region of increased angular fluorescence and increased angular SS or FS relative to the background debris region may be bacteria in the sample, preferably mycobacteria, such as *M. tuberculosis*, *M. smegmatis*, *M. bovis*, *M. avium*, *M. fortuitum* and so forth. Preferably, the mycobacteria is *M. tuberculosis* or alternatively species of *Staphylococcus* or *Clostridium*.

The absence of events within a region of increased angular fluorescence and increased angular SS or FS relative to the background debris region may be indicative that the subject does not have tuberculosis.

The presence of events within a region of increased angular fluorescence and increased angular SS or FS relative to the background debris region may be indicative that the subject has tuberculosis.

The subject may be a human or other animal.

The background debris may include lysed cells, mucous, saliva and the like, and is typically present in sputum samples from both tuberculosis-positive and tuberculosis-negative subjects.

The sputum sample may be liquefied and/or decontaminated and/or inactivated prior to performing the flow cytometry.

Preferably, the sputum sample is deactivated. The inactivation agents may be selected from the group comprising IDP, Xpert SR buffer, heat, and the addition of lysozyme.

The sputum sample may be treated with a nucleic acid binding dye, such as auramine O, SYTO dye or propidium iodide.

The flow cytometry may be performed using beads.

The bacteria may be pre-labelled with a bead, ligand and/or specific antibody, all of which may be fluorescently labelled and detected by flow cytometry, in order to aid the identification of events in the angular region.

The method may further include the step of liquefying and/or decontaminating and/or inactivating the sputum sample prior to performing the flow cytometry. The sputum sample may be cultured prior to liquefying and/or decontaminating and/or inactivating.

The absorbent material may be selected from the group comprising a filter card, a filter paper, a swab, a bead, a sample tanker and cotton. The absorbent material ideally includes bacterial field strains, reference strains or negative controls. In particular, the absorbent material may find use for verification of the method and/or calibration of the method and/or use as an external quality control assessment (EQA) tool.

The method of diagnosis may be selected from the group comprising GenoType® MTBDR and MTBDRplus™, INNO-LiPA™ Rif.TB, GeneXpert™ MTB/RIF, GeneXpert™ MRSA, GeneXpert™ *C. difficule*, loop-mediated isothermal amplification technology, COBAS TaqMan™ MTB, Gen-Probe Amplified *Mycobacterium Tuberculosis* Direct Test (AMTD) and enhanced AMTF (E-AMTD), LightCycler™ *Mycobacterium* detection kit (LCTB), Seeplex TB Detection Kit, BD-ProbeTec™ Direct and the semi-automated ProbeTec™ ET system and the Abbott LCx.

DETAILED DESCRIPTION OF THE INVENTION

The applicant has now developed a method for the rapid identification of bacteria. A person of skill in the art will appreciate that the method of identification can be extended to all gram-positive bacteria, including Actinobacteria, Firmicutes and Tenericutes. In particular, the applicant has developed a method for identifying Actinobacteria, more specifically mycobacteria, for use in the diagnosis of tuberculosis (TB), comprising subjecting a sputum sample from a subject to flow cytometry and analysing the SS or FS and fluorescence properties of the sample. The mycobacteria (such as *M. tuberculosis, M. smegmatis, M. bovis, M. avium, M. fortuitum* and so forth) can be identified directly from sputum using this high throughput platform to provide a result on the same day or within 24 hours. The subject may be a human or an animal (examples of animals are bovine species, livestock, birds, swine, cattle, dogs and wild animals such as buffalo, deer and lion).

Flow cytometry is a technology that identifies particles such as red blood cells, white blood cells, bacteria and chromosomes which are freely suspended. Through the use of focused laser light, each event or particle can be detected by the amount of the incident light that is scattered when the particle interrupts the laser beam. The advantage of this is the speed at which this analysis is performed and that is can be performed on inactivated non-viable organisms. Several thousand events can be analysed per second. Flow cytometry is currently used in pathology services for tests such as CD4 counting, where the number of CD4 cells in a person can describe the immunological status and be used in measuring an HIV infected persons progression to AIDS. This technology is widely used in South Africa in about 60 laboratories nationally placed in tertiary and secondary (district hospital) settings. Performing the new TB diagnostic method will therefore not require any additional equipment or highly skilled staff, thus making the technique affordable and readily available.

Flow cytometry can only be performed on particles that are freely suspended and there have been several descriptions of bacteria analysed by flow cytometry (2, 8), and recently its application to *M. tuberculosis* (1, 3-7). Most of these studies, however, have analysed isolated bacteria grown from culture and none of them have analysed bacteria directly from sputum for rapid diagnosis.

Figure 1:
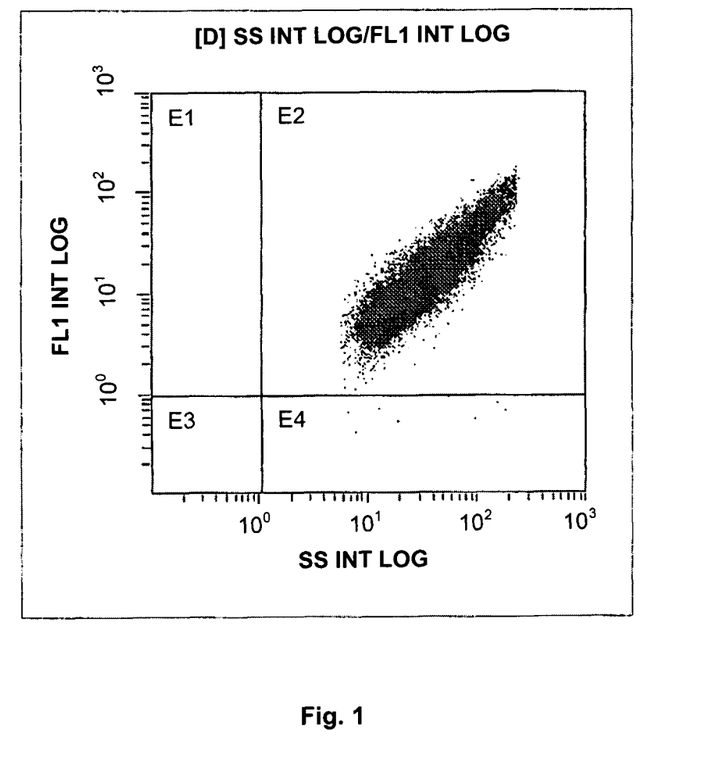
FIG. 1: shows a flow cytometry dot plot showing FL1 vs SS of *Mycobacteria smegmatus*, a close relative to *M. tuberculosis*. The picture shows the typical angular shape of the bacteria population with increasing FL1 and SS characteristics.

The present invention identifies the mycobacteria directly from the sputum sample, which still contains other cells and particles. Isolated mycobacterial populations from culture can be identified by flow cytometry as having a typical angular shape with increasing FL1 and SS (or FS) characteristics, and the applicant has been able to identify *M. smegmatis* and *M. tuberculosis* populations as having this pattern at concentrations of bacteria as low as 10 bacteria/ml (FIG. 1).

The applicant has found that using this angled region, bacteria have variable and greater fluorescence than background cells and variable and greater SS or FS than background cells, and this combination and the angled region can be used to identify the bacteria in a sputum sample. Taken together, the fluorescence and SS or FS parameters of the bacteria are greater than the fluorescence (and in particular FL1) and SS pattern of the background debris in sputum (e.g. lysed cells and mucous). More particularly, drawing a region at an angle of about 40° to about 50°, and preferably at about 45°, on a fluorescence versus side scatter plot will identify the bacteria if they are present in the sputum sample.

Beads can be added to the sputum sample. The beads may be in the range of about 0.8 µm to about 12 µm in diameter, and preferably about 1 µm in diameter.

The sputum sample may be treated with a dye, such as auramine O, SYTO dye, propidium iodide or any other suitable nucleic acid binding dye and/or a labelled ligand and/or a labelled antibody.

Other parameters that can be used to improve the detection of the bacteria in the sputum sample include:
  using a Gallios flow cytometer from Beckman Coulter, which has added features such as wide angled FS designed to improve the detection of small particles;
  using a Gallios flow cytometer that has the ability to measure time of flight (TOF) to discriminate single from doublet particles;
  using 1 µm beads to set a size threshold; and
  including a negative live gate—also set at an angle to eliminate the number of events reported from the debris region.

The latter may improve the sensitivity of the assay of the present invention, without limiting its application to other instrument platforms. In addition to these instrument parameters, there are several other features to this protocol that can also increase the sensitivity of bacterial detection against background debris. For example, the background debris in the flow cytometry sample tube can be reduced by preventing precipitation between nucleic acid binding dyes and phosphate buffers, and preventing precipitation between peracetic acid and dyes or buffers.

Figure 2:
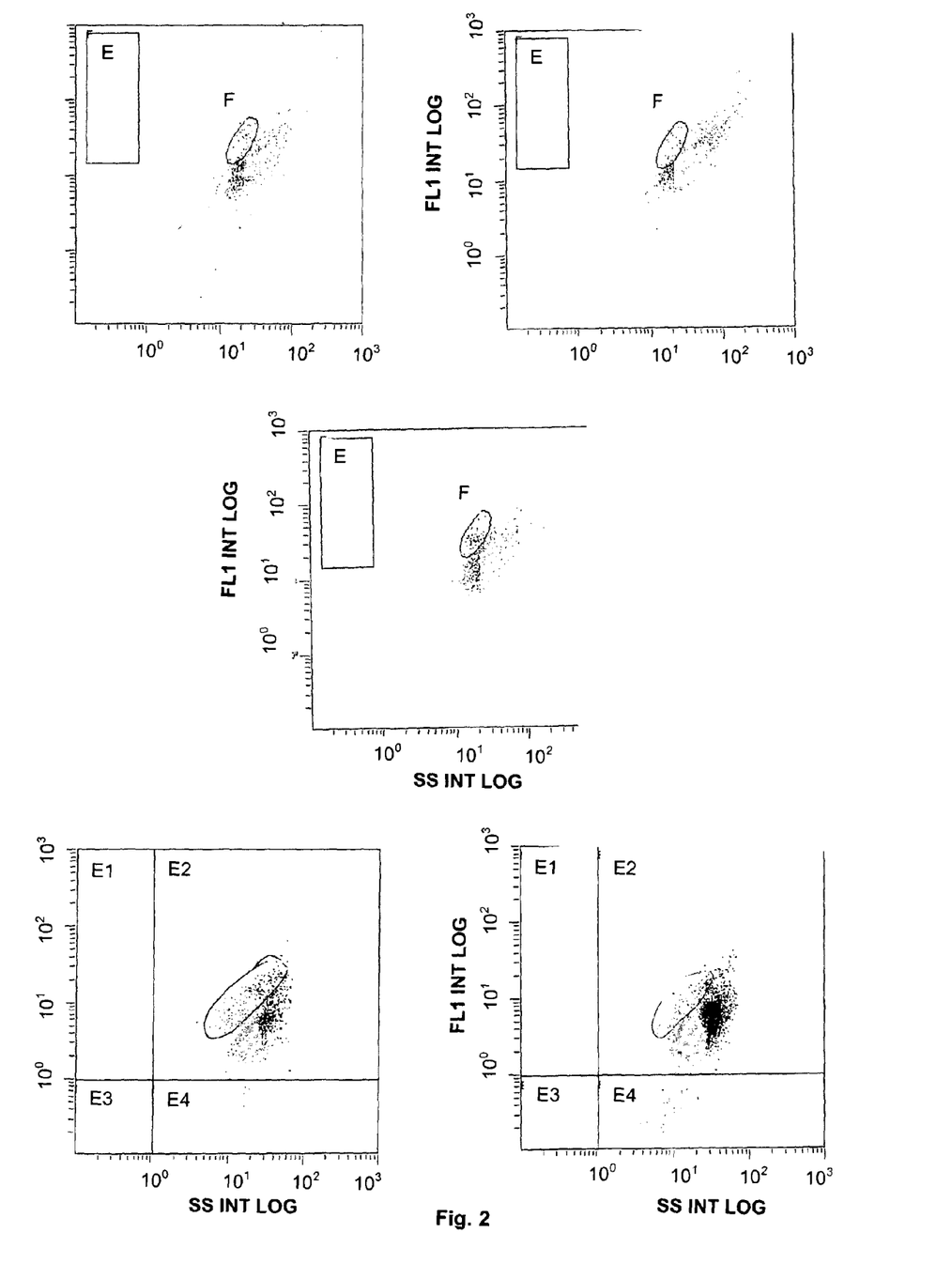
FIG. 2: shows flow cytometry dot plots of smear positive and culture positive sputum samples analysed to identify the presence of mycobacteria using an angular region based on increasing FL1 and increasing SS characteristics of the bacteria compared to the background debris.
Figure 3:
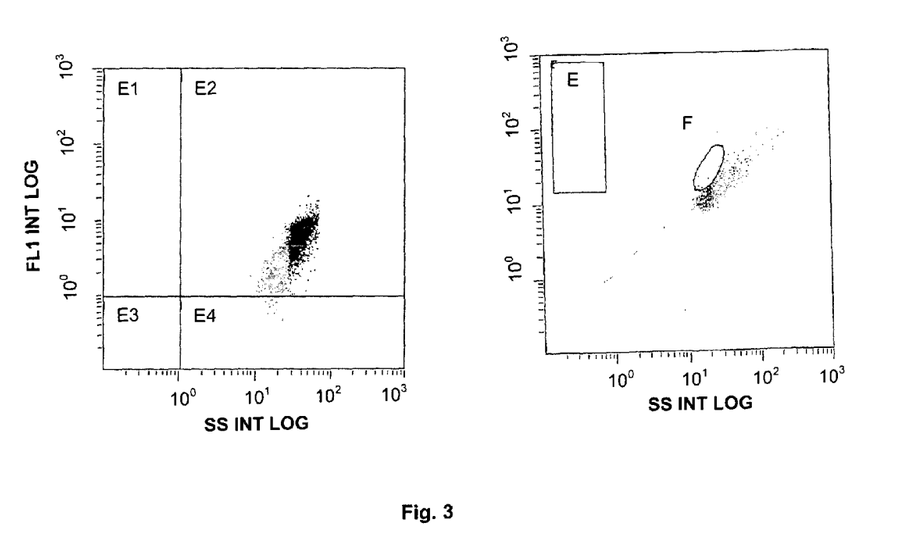
FIG. 3: shows a flow cytometry dot plot of a smear negative, culture negative sample using this protocol. One plot shows the angular region with no events, and another sample shows no angular region to illustrate the absence of bacterial events and only debris.
Figure 4:
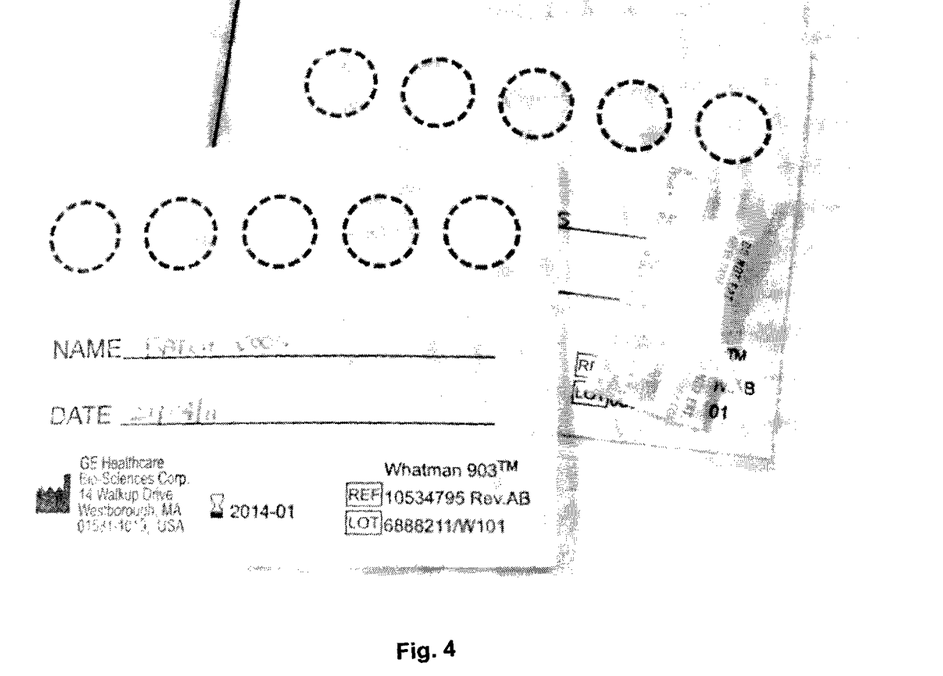
FIG. 4: shows a sample of the DCS on filter cards and in plastic transport bags with desiccant sachets. Four DCS/card containing inactivated *M. tb* culture are visualised by the blue dye.

The method of the invention for identifying the bacteria in sputum samples is shown in FIG. 2, where 5 plots show examples on TB sputum smear positive and culture positive samples. The x-axis is SS and the y-axis is FL1. Regions are drawn in the angular shape to identify the bacteria against the background sputum debris. The bacteria (in this case *M. tuberculosis*) are easily identified in the region with increased angular fluorescence and increased angular SS. The events outside of this angular region are the background debris from the sputum. FIG. 3 further shows this protocol applied to a smear negative, culture negative sample, and here no bacteria can be identified with the characteristics mentioned above.

Although the method of the present invention is currently non-specific and does not identify the bacteria specifically as *M. tuberculosis* or detect drug sensitivity, it can be used as a high throughput screening method. Once prepared, 32 samples are loaded into a flow cytometry instrument and analysis of all 32 samples can be performed within 40 minutes. This becomes particularly useful for HIV clinicians needing to ensure that a patient is TB negative before initiating anti-retroviral therapy (ART). In addition, it is not reliant on amplification for detection and will cost about the same or less than a PLG (NHLS standard test) CD4 count.

The method of the invention can be performed as a screening test to identify the presence or absence of bacteria in sputum samples. Those with a "flagged" or positive result can then be further processed by the GeneXpert to then yield a positive *M. tuberculosis* with/out rifampin resistance/sensitivity result. In total, this will reduce the costs of the cartridge-based PCR GeneXpert and only limit it to positive confirmation including the rifampin result. This therefore eliminates the need for smear and culture testing and will enable more laboratory centres currently performing flow cytometry CD4 testing to perform decentralised TB diagnostics. It will be appreciated that as the specific type of bacterium is not identified, that the method of using flow cytometry can be performed to identify the presence of any bacterium, which can then be further analysed by a bacterium-specific method. For example, species of *Staphylococcus* and *Clostridium* may also find application using this method, as the GeneXpert MRSA and GeneXpert *C.difficule* have been developed.

It is apparent that the use of flow cytometry in accordance with the current invention offers at least the following advantages over traditional methods:
  (i) flow cytometry rapidly (>1000 events/second) identifies inactivated single whole bacterial events thereby circumventing conventional, time consuming colony forming unit enumeration methodologies; and
  (ii) bacterial concentrations <10 events/µl can be accurately enumerated (using calibrated microspheres) i.e. flow cytometric event enumeration can be performed below the minimum McFarlane concentrations ($1 \times 10^7$ bacteria/ml).

This invention further describes a program that has being developed by the Department of Molecular Medicine and Haematology Research Diagnostic Division (University of Witwatersrand, Johannesburg) to address all the concerns around the functional implementation of the GeneXpert MTB/RIF assay. In particular, methods to establish a sample database for calibration and verification of the results obtained for each GeneXpert instrument installed at the various geographical locations, and for generating EQA programs to ensure on-going quality testing were developed. In particular, this invention describes the application of a method for identifying mycobacteria in a sample, in particular *M. tuberculosis* bacillary counts, as events detected by flow cytometry in accordance with the method of the current invention. The mycobacteria may be used directly from a sputum sample or may be cultured and harvested. The mycobacteria are then inactivated using standard methods and quantified via flow cytometry before being spotted onto filter cards.

The clear advantage of using these dried culture spots (DCS) are that they are easily, and with limited biohazardous risk, transported to any GeneXpert MTB/RIF testing site, cut and tested as per patient samples.

DCS can thus be bulked up and distributed to each centre where the GeneXpert MTB/RIF assay is being performed to diagnose TB. In particular, the generated DCS finds application for calibration and/or maintenance and/or verification of the GeneXpert instrument on which the assay is performed and thus the results obtained. DCS of various clinical (and ATCC) strains, non-*mycobacterium tuberculosis* (NTM) and negatives will find use for monthly/annual EQA monitoring. This program has the potential for scale-up to meet the needs of national programs as well as support surrounding countries.

A challenge for the implementation of the Xpert MTB/RIF assay in a national program was the placement of instruments followed by verification and on-going assay performance monitoring. As part of the South African National Health Laboratory Services (NHLS) national priority program for the GeneXpert MTB/RIF roll out, 31 GeneXpert (Gx) instruments were installed throughout the country in all 9 provinces, between March and April 2011. This totalled 286 Gx modules requiring verification before deemed "fit for purpose" to report results on patient specimens.

The applicant envisaged that the only way to achieve this was through an EQA program. The difficulty with such a program for TB is the infectious nature of testing material. This is the greatest challenge, which the applicant overcame with the use of inactivated *M. tuberculosis* material and easier transportation of material by DCS. However the challenge in using inactivated *M. tuberculosis* culture material is the inability to determine the concentration of bacteria (cfu/ml) which cannot be cultured once the bacteria are inactivated. The applicant successfully overcame this challenge with enumeration by flow cytometry.

The applicant has thus succeeded in the following manner: (1) the development of the DCS material (including DCS stability) for an *M. tuberculosis* EQA program, (2) the enrolment of new Xpert MTB/RIF testing sites (through verification); and (3) scale-up of the protocols for on-going EQA activities that (4) which can be routinely offered by the NHLS once developed.

The invention will now be described in more detail with reference to the examples described below. These examples, however, are not intended to limit in any way the scope of the invention. For example, instead of using side scatter and FL1, it would also be possible to use forward scatter and another fluorescence channel, for example, when using another dye. Furthermore, it will be appreciated that the term "filter card" encompasses any means upon which the mycobacteria can be spotted and dried and any surface with absorbent properties for retaining the spotted bacteria. Typically, the term filter card would include a swab, paper, cotton wool, sample tanker, tissue paper or the like.

EXAMPLES

1. Overview of Quantitation of *M. tuberculosis* Bacterial Events Using Flow Cytometry a) Sputum was harvested from a subject.
b) Standard methodology using NaOH-NALC-Sodium Citrate was used to liquify and decontaminate sputum.
c) This was followed by bacterial inactivation using peracetic acid: 1 volume of processed sputum is added to 1 volume of 4% peracetic acid to make a final concentration of 2% peracetic acid.
d) After 30 mins incubation at room temperature in a bioflow, the tubes were removed from under the bioflow and worked with on the bench.
e) The peracetic acid was removed by washing in water followed by centrifugation and resuspension in water.
f) 50 μl of this solution was added to 1 ml auramine O stain (nucleic acid binding dye) and incubated for 5-10 mins.
g) Flow cytometry was performed on this sample according to the following design protocol:
   i. Using 1 μm flow cytometry beads, the threshold on size was set to just below this 1 μm level so the beads were visible on a FS vs SS dual plot.
   ii. On a second plot FL1 (fluorescence 1 on the y-axis) vs SS (x-axis) a region at a 45° angle was drawn to identify the bacterial events.
   This region was placed to identify bacterial events which have variable (increasing) SS and variable (increasing) fluorescence, hence a 45° angled region.
   This angled region allows for clear separation of bacterial events from debris.
   The debris is made up of lysed cells, mucous etc from sputum samples.

2. Growth of *M. tuberculosis* in Liquid Culture

The *M. tuberculosis* used for preparing cultures was obtained from three sources: (1) pooled samples from microbial growth incubation tubes (MGIT) of RIF sensitive clinical isolates obtained from the Contract Laboratory Services (CLS, Johannesburg, South Africa) and tested by the MTB-DRplus (Hain Life Sciences) line probe assay, (2) pooled MGIT tubes from ATCC (American Type Culture Collection) strain S-MYCTU-02-P2 and MYCTU 15 and (3) laboratory strain H37Rv (ATCC) grown for single cell organism suspensions.

The MGIT method used modified Middlebrook 7H9 broth base, supplemented with MGIT Growth Supplement and PANTA (Becton Dickinson) and incubated at 37° C. up to 42 days in a BACTEC cabinet (Becton Dickinson). Positive cultures were subject to Ziehl Neelsen staining to confirm the presence of Acid Fast Bacilli (AFB). For single-cell suspensions, the H37Rv stain was grown from laboratory freezer stocks in 8 ml Middlebrook 7H9 broth (Difco, Detroit, Mich.) supplemented with 0.2% glycerol, Middlebrook oleic acid-albumindextrose-catalase (OADC, Merck) enrichment, and 0.05% Tween 80, to prevent clumping, for 5 days in 25 ml tissue culture flasks (Greiner Bio-one). Thereafter, this preculture was inoculated into 200 ml of the above mentioned media in 550 ml tissue culture flasks and grown for 10 days stationary at 37° C.

3. Inactivation of the Cultured *M. tuberculosis*

Bacteria were subjected to a range of chemical and enzymatic activation agents including IDP, Xpert SR buffer, heat, low concentrations of lysozyme, or a combination thereof to ensure complete killing of organisms along with maintenance of bacterial structure and composition, an essential requirement for consistent and accurate determination bacterial counts by flow cytometry. This is also critical for use in conjunction with the GeneXpert MTB/RIF assay as whole bacteria are required for PCR.

For example, in brief the MGIT cultures from the laboratory strain S-MYCTU-02-P2 and MYCTU 15 and clinical isolates were pooled (strains kept separate), centrifuged to pellet the cells and resuspended in 40 ml PBS followed by addition of 80 mls (2:1 ratio of buffer to culture) of the GeneXpert sample reagent (SR) buffer (provided in the kit). For the H37Rv strain, 200 ml of culture was harvested by centrifugation at room temperature for 10 min at 3500×g. Cells were resuspended in sterile PBS to a final volume of 40 ml followed by addition of 80 ml SR buffer (2:1 ratio of buffer to cells). Both MGIT grown and H37Rv strain culture material was incubated in SR buffer for 2 hrs at room temperature, with intermittent mixing to render all bacteria inactive and safe for flow cytometry, without any adverse effects to the bacterial size. The inactivated material was then washed twice with sterile PBS and resuspended in a final volume of 10 ml (MGIT) and 40 ml (H37Rv) PBS. If the dye auramine O was to be used, the inactivated *M. tuberculosis* were washed and re-suspended in distilled water, as the SR buffer caused precipitation and quenching of the dye.

For confirmation of inactivation, washed cultures (0.5 ml) were re-inoculated into new MGIT tubes. MGIT's were incubated in BACTEC cabinets for a maximum of 42 days before the inactivated bulk stock was enumerated by flow cytometry.

4. Flow Cytometric Bacterial Quantification

If the bacterial stocks showed any visual clumping, they were declumped (32) by passaging ~10 times through a 26-gauge needle, and sonication for 2 min in a table top ultrasonic cleaning system (Fisher Scientific). Volumes (ranging from 10 μl to 50 μl) of SR inactivated, washed and concentrated *M. tb* was added to 1 ml PBS in blue flow cytometry tubes (Beckman Coulter). This was followed by the addition of 100 μl Auromine O stain (Diagnostic Media Production, NHLS, South Africa) and 50 μl Flow Count microspheres (10 μm)(Beckman Coulter) to each flow cytometry tube which was then immediately analysed on an FC500 flow cytometer per manufacturer instructions (Beckman Coulter). For preliminary protocol design, 1 μm microspheres (Beckman Coulter) were used to set the size threshold (discriminator) and amplification gains of the light scatter parameters. Dilutions (1:4 to 1:200) of the stock cultures were prepared in PBS before flow cytometry enumeration. Two dimensional scatter plots applied were: FS (vertical axis) versus SS (horizontal axis) to identify the bacterial events close to 1 μm in size; a second plot FL1 (530 nm) versus SS to identify bacterial events with increased fluorescence; and a third plot using FS linear versus FL2 (570 nm) to identify flow count microspheres for automatic event enumeration through the CXP software (Beckman Coulter). Regions were applied to identify the bacterial events. Once the concentrations of inactivated *M. tb* culture stocks were quantified by flow cytometry, various concentrations were analysed using the Xpert MTB/RIF assay.

5. Testing on the Xpert MTB/RIF Assay

The Xpert MTB/RIF hemi-nested real-time PCR assay (Cepheid, Sunnyvale, Calif.) amplifies the 81 by region of the Rif-resistance determining region (RRDR) of the rpo B gene from region 507-533. Due to its real-time PCR nature, results reported from the Xpert MTB/RIF assay are both qualitative and semi-quantitative. The former describes the presence or absence of *M. tb* and whether Rif resistance was detected. The latter describes the cycle threshold (Ct) values for five probes (A-E) and the internal control. The Ct values are reported in the semi-quantitative categories for 6 Ct as very low, low, medium and high.

Dilutions of the *M. tb* inactivated, washed and enumerated culture stock were added to 2.0 ml SR buffer directly into the Xpert MTB/RIF cartridge sample port, and cartridges were placed into the GeneXpert instrument for processing. The Ct ranges for the semi-quantitative categories are: high are <16; medium 16-22; low 22-28 and very low >28 as per the manufacturer's instrument and assay specification. The Xpert MTB/RIF Ct values for probe A were compared to the flow cytometry enumeration score and dilutions that generated a medium (Ct value between 16 and 22) qualitative Xpert MTB/RIF result was then used for preparing the DCS.

6. Preparation and Evaluation of DCS

DCS were prepared by spotting 25 μl amounts of inactivated culture material onto Whatman 903 filter cards (Merck) together with 2 μl of DNA loading dye (Sigma-Aldrich) per spot for visualization purposes (FIG. 4) and dried for at least 1 hour at room temperature. A sample spot from each DCS batch manufactured was tested on the Xpert MTB/RIF before releasing for distribution to the sites. The DCS cards were placed in sealed plastic bags with a desiccant sachet (Sigma-Aldrich) and couriered (n=16), or hand delivered (n=9), or surface mailed (repeat DCS to 4 sites) to each site. At sites, each spot was cut using a sterile pair of scissors into a 50 ml standard laboratory Nunc centrifuge tube (AEC Amersham) and 2.8 ml SR buffer (to ensure there was sufficient 2 ml to pipette into the Xpert MTB/RIF cartridge after the DCS incubation) was added to the tube. The tubes were vortexed (or hand shaken by swirling vigorously) and left to incubate at room temperature for 15 minutes with intermittent mixing as per sample processing protocol. After 15 minutes, 2 ml of the mixture was transferred to the Xpert MTB/RIF cartridge and tested on the GeneXpert as per the manufacturer's instructions. After testing of each GeneXpert module at the sites, the results for each module were selected to be archived, and the Gene Xpert Archived files (.gxx) were emailed to a central co-ordinator for evaluation. Once the results were received by the co-ordinator, these were imported into the local GeneXpert Database and then exported to a comma separated value (.csv) file for data capturing and reporting purposes. A detailed SOP was disseminated to the sites delineating the archiving and mailing process for the EQA program.

7. Statistical Analysis

Qualitative and quantitative Ct values generated by the Xpert MTB/RIF assays were documented for each GeneXpert module tested per batch of DCS. The mean, standard deviation and coefficient of variation were calculated for each batch using the probe that first reached the amplification cycle threshold. These are also represented graphically in frequency distributions. The relationship between the Flow cytometry enumeration score and the Xpert MTB/RIF assay Ct is quantitated by linear regression.

Figure 5:
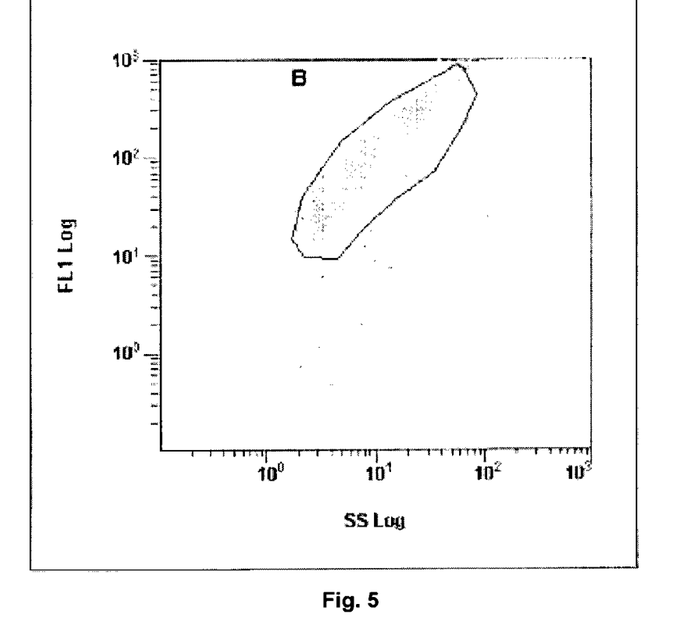
FIG. 5: shows a flow cytometry scattergram using side scatter threshold and enumerating bacterial events identified in region B based on their increased angled fluorescence of auramine and increased angled side scatter of incident laser light. Events outside region B show minimal background debris.
Figure 6:
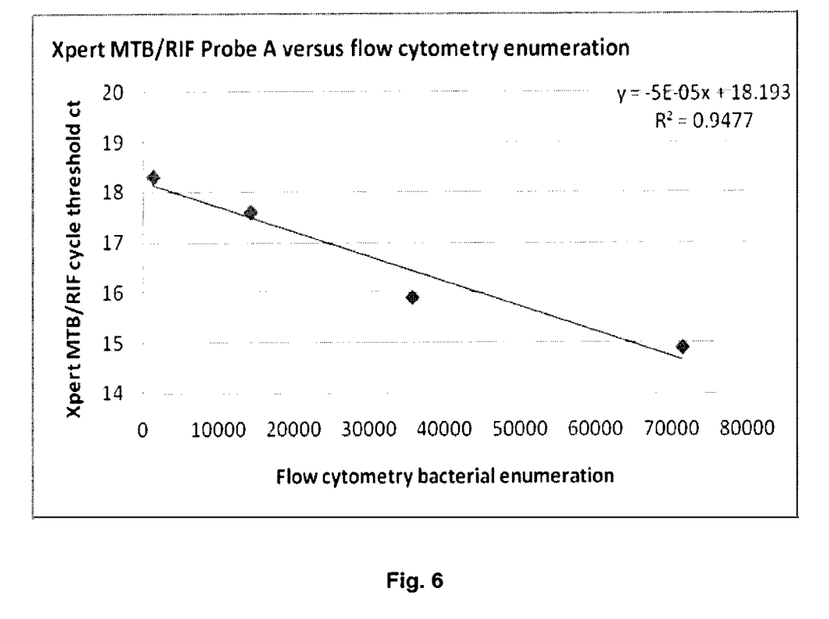
FIG. 6: shows a plot of the Xpert MTB/RIF amplification cycle thresholds (vertical axis) compared to the flow cytometry enumerated culture concentrations (horizontal axis) for single cell culture prepared H37Rv *M. tb*.
Figure 7:
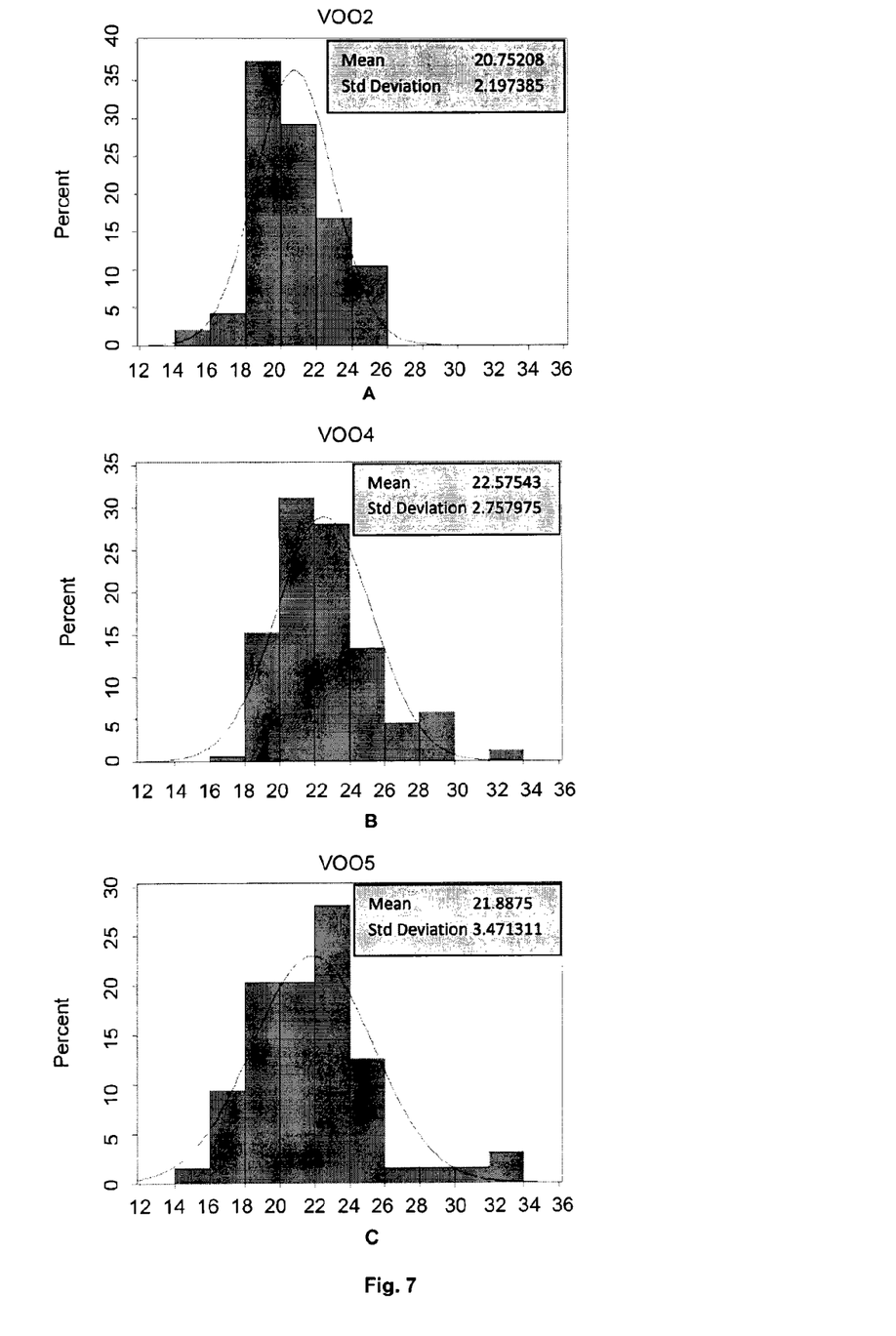
FIG. 7: shows the frequency distributions overlaid with normal curves of the Ct values for probe A from the three dried culture spots (DCS) batches. The standard deviation and mean Ct values are represented in the legends.

8. *M. tb* Bulk Culture Manufacture, Inactivation and Enumeration by Flow Cytometry All cultures prepared for DCS after 2 hours incubation with SR buffer showed no growth in MGIT up to 42 days confirming inactivation. The prepared pools of MGIT cultures showed clumping of *M. tb* due to characteristic cording, which necessitated sonication before flow cytometric enumeration, whereas the cultures grown in the presence of glycerol and Tween 80 did not require pre-sonication and yielded single cell suspensions more readily identified by flow cytometry (FIG. 5). Flow cytometry analysis applying a SS threshold appeared to yield better enumeration scores than the same analysis performed after applying a FS threshold. FIG. 6 shows a good relationship ($R^2$=0.948) between flow cytometry enumeration and Xpert MTB/RIF amplification Ct for probe A on the bulk culture prepared for single cell suspension of H37Rv.

SR buffer did cause precipitation (evident by higher debris counts by flow cytometry) and visual quenching of auramine dye used for fluorescent identification of bacteria by flow cytometery and therefore the bacterial cultures required washing and re-suspension in distilled water before addition of auramine and analysis by flow cytometry. The SR inactivation after 2 hours did not affect bacterial size and 1 μm beads could be used in the flow cytometry protocol to accurately identify the *M. tb* bacterial events.

tivity (Table 1 provides a summary of results). The six errors reported were GeneXpert error codes 5011 (n=5) and 5007 (n=1). This overall error rate of 2.19% (6/274) showed error codes attributed to a combination of user (incorrect amount of reagent inserted) or cartridge errors (failed fluid transfer or loss of tube pressure) and are not indicative of the failure of a DCS. Two sites repeated DCS testing on the error modules and reported positive results (passed), additional DCS have been sent to the remaining sites requiring module re-testing.

Probe A was the first probe to reach the amplification cycle threshold and had an average Ct value on the upper limit of the medium/low boundary of 22. A range across 6 Ct values identifies the categories (low to medium) for probe A, and the standard deviations of all three DCS batches were ≤3.47 Ct, indicating good precision of the DCS batches with low variability. Frequency distributions in FIG. 4 illustrate the spread of DCS Ct values around the mean for probe A for the three batches. The greatest variability was found in batch V005 (14.4% CV) from the single-cell generated culture.

In addition to the quantitative outcomes of the DCS GeneXpert module verification, the DCS program also identified other issues that could assist with the implementation going forward as detailed in Table 3. Non-conformance was considered as any site which did not submit the correct file format (archived .GXX format) for EQA reporting. Disruption of the DCS filter paper material is not necessary for DCS processing, but 3 sites that tried to disrupt the DCS filter paper did not show any discrepancies in results, other than on average a lower Ct values for probe A. The lower Ct value may be due to the re-suspension in the SR buffer of more bacteria available for amplification. No result returns have indicated sites that need investigation for overall Gx operations and conformance to standard operating procedures.

TABLE 1

The performance of the three DCS batches on 268 Gx modules.

| | DCS batch number | | |
|---|---|---|---|
| | V002 | V004 | V005 |
| *M. tb* bulk culture material | MGIT clinical controls: *M. tb* Rif sensitive | MGIT ATCC strain: *M. tb* Rif sensitive | H37 laboratory strain: *M. tb* Rif sensitive |
| Number of Gene Xpert modules tested by DCS | 49 number all *M. tb* Rif sensitive | 173 number all *M. tb* Rif sensitive (161 returned results) | 64 number all *M. tb* Rif sensitive |
| Number of errors | 1 (5011) (2%) | 4 [5011 (3), 5007 (1)] 2.5% | 1 (5011), 1.6% |
| Number of DCS for statistical analysis | 48 | 157 | 63 |
| Percentage testing in any one qualitative category | Very low: 0%<br>Low: 26.53%<br>Medium: 69.39%<br>High: 2.04% | Very low: 5.1%<br>Low: 47.13%<br>Medium: 47.77%<br>High: 0% | Very low: 6.25%<br>Low: 42.19%<br>Medium: 48.44%<br>High: 1.56% |
| Mean Ct for Probe A | A: 20.75 | A: 22.58 | A: 21.89 |
| Standard deviation of the Ct for probe A | A: 2.20 | A: 2.76 | A: 3.47 |
| Coefficient of variation of the Ct for Probe A | 10.6% | 12.22% | 15.86% |

9. Performance of DCS at Testing Sites for Verification of the Gene Xpert Instruments Performing the Xpert MTB/RIF Three DCS batches were manufactured for verification of 31 GeneXpert instruments {Gx Infinity-48 (n=1); Gx16 (n=9); Gx4 (n=21)}. A total of 286 DCS were distributed to sites, and results received to date for 274 DCS. Six testing errors were reported and the remaining 268 DCS generated anticipate results with 100% *M. tb* positivity and Rif sensi- South Africa faces enormous health care challenges with more than one million people currently receiving HIV anti-retroviral treatment, the TB incidence is 941 per 100 000 population and 9070 cases of multidrug resistant TB (MDR TB) were reported in 2009. In 2010 the total number of sputum smears conducted in 244 NHLS laboratories over the nine provinces was ~4.7 million tests (average of 2 smears per patient). Based on this in-country data it is estimated the pilot Gene Xpert implementation with 30 Gx instruments only had an 11.1% coverage, and that >250 more Gx instruments are required for full coverage. Lessons learned from this countries rapid path to scale (within 1 year) for HIV viral load testing through the development of a pre-qualification panel and training for 20 new laboratory sites totalling ~50 HIV viral load molecular testing instruments can similarly be followed for the Gene Xpert implementation plan.

The major challenge encountered with any EQA program for TB is the infectious nature of material to be tested. The applicant has shown that through the use of inactivated *M. tuberculosis* coupled with easier transportation of material by DCS that an EQA program can be safely provided at both laboratory and clinic testing sites for the Xpert MTB/RIF. The DCS material proved 100% successful for verifying Gx instruments. The DCS also highlighted error codes and their frequencies that national programs can expect as the least amount of invalids (2.1%) to include in their program costs due to Gx module performances. Other areas requiring monitoring such as turnaround time from specimen receipt to result reporting, could also be monitored with the DCS program, and identify problem sites.

The applicant envisages that future design of the components of the EQA program for the Xpert MTB/RIF assay could be similarly based on LPA programs using one pansusceptible strain, one RIF-monoresistant strain with a common rpoB mutation, one MDR strain, one NTM strain and a negative. Using DCS each of these can be placed on one card and distributed to all sites 3 or 6 monthly (depending on DCS stability outcomes testing underway) where each spot contains a different strain. Further, the applicant regards the current technology as forming the platform to develop other aspects to be included in the EQA specific to the Xpert MTB/RIF. These aspects include monitoring the rate of invalid tests, the RIF mutation frequencies (or mixed drug resistant/sensitive profiles) and list of specimens tested (and technician/health care worker performing the test) per reagent batch. These processes require innovative information technology solutions, as the Gene Xpert instruments will require interfacing to laboratory information systems, and this may also be the conduit to returning EQA results not captured by a laboratory information system.

REFERENCES

1. Burdz, T. V., J. Wolfe, and A. Kabani. 2003. Evaluation of sputum decontamination methods for *Mycobacterium tuberculosis* using viable colony counts and flow cytometry. Diagn Microbiol Infect Dis 47:503-9.
2. Ibrahim, P., A. S. Whiteley, and M. R. Barer. 1997. SYTO16 labelling and flow cytometry of *Mycobacterium avium*. Lett Appl Microbiol 25:437-41.
3. Moore, A. V., S. M. Kirk, S. M. Callister, G. H. Mazurek, and R. F. Schell. 1999. Safe determination of susceptibility of *Mycobacterium tuberculosis* to antimycobacterial agents by flow cytometry. J Clin Microbiol 37:479-83.
4. Pina-Vaz, C., S. Costa-de-Oliveira, and A. G. Rodrigues. 2005. Safe susceptibility testing of *Mycobacterium tuberculosis* by flow cytometry with the fluorescent nucleic acid stain SYTO 16. J Med Microbiol 54:77-81.
5. Pina-Vaz, C., S. Costa-Oliveira, A. G. Rodrigues, and A. Salvador. 2004. Novel method using a laser scanning cytometer for detection of mycobacteria in clinical samples. J Clin Microbiol 42:906-8.
6. Reis, R. S., I. Neves, Jr., S. L. Lourenco, L. S. Fonseca, and M. C. Lourenco. 2004. Comparison of flow cytometric and Alamar Blue tests with the proportional method for testing susceptibility of *Mycobacterium tuberculosis* to rifampin and isoniazid. J Clin Microbiol 42:2247-8.
7. Soejima, T., K. lida, T. Qin, H. Taniai, and S. Yoshida. 2009. Discrimination of live, anti-tuberculosis agent-injured, and dead *Mycobacterium tuberculosis* using flow cytometry. FEMS Microbiol Lett 294:74-81.
8. Steen, H. B., E. Boye, K. Skarstad, B. Bloom, T. Godal, and S. Mustafa. 1982. Applications of flow cytometry on bacteria: cell cycle kinetics, drug effects, and quantitation of antibody binding. Cytometry 2:249-57.

The invention claimed is:

1. A method for determining performance of a diagnostic method, the method comprising:

(i) culturing a sputum sample from a subject, wherein the sputum sample comprises bacteria;

(ii) inactivating the cultured sputum sample;

(iii) quantifying the bacteria in the inactivated sample to obtain a first score;

(iv) spotting the inactivated sample onto an absorbent material;

(v) quantifying the bacteria in the spotted sample using a diagnostic method to obtain a second score;

(vi) determining the performance of the diagnostic method based on a comparison between the first score and the second score.

2. The method of claim 1, wherein the bacteria are quantified using flow cytometry or PCR.

3. The method of claim 1, wherein the bacteria are mycobacteria selected from the group consisting of *Mycobacterium tuberculosis, Mycobacterium smegmatis, Mycobacterium bovis, Mycobacterium avium* and *Mycobacterium fortuitum.*

4. The method of claim 1, wherein the sputum is treated with a nucleic acid binding dye.

5. The method of claim 1, wherein the bacteria are prelabelled with a bead, a ligand or an antibody, and wherein the bead, ligand or antibody optionally comprises a fluorescent label.

6. The method of claim 1, further including the step of liquefying and/or decontaminating the sputum sample prior to quantifying the bacteria.

7. The method of claim 1, wherein absorbent material is selected from the group consisting of a filter card, a filter paper, a swab, a bead, a sample tanker and cotton, the absorbent material optionally comprising bacterial field strains, reference strains or negative controls.

8. The method of claim 1, wherein the absorbent material is used in conjunction with a method of diagnosis of tuberculosis for verification of the method and/or calibration of the method and/or use as an external quality control assessment (EQA) tool.

* * * * *